(12) United States Patent
Bestetti et al.

(10) Patent No.: US 6,270,475 B1
(45) Date of Patent: Aug. 7, 2001

(54) PORT BODY FOR THE ADMINISTRATION OF DRUGS

(75) Inventors: Gilberto E. Bestetti, Köniz; Thomas Frei, Lützelflüh; Andreas Reinmann; Daniel Piller, both of Bern, all of (CH)

(73) Assignee: Diesetronic Licensing AG, Burgdorf (CH)

(*) Notice: Subject to any disclaimer, the term of this patent is extended or adjusted under 35 U.S.C. 154(b) by 0 days.

(21) Appl. No.: 09/048,682

(22) Filed: Mar. 26, 1998

(30) Foreign Application Priority Data

Mar. 26, 1997 (CH) .......................................... 19970729/97

(51) Int. Cl.⁷ .......................... A61M 11/00; A61M 5/32; A61M 25/16
(52) U.S. Cl. ..................... 604/93.01; 604/175; 604/533
(58) Field of Search .............................. 604/93, 174, 175, 604/244, 905, 533

(56) References Cited

U.S. PATENT DOCUMENTS

| | | | |
|---|---|---|---|
| 3,783,868 | * | 1/1974 | Bokros .................................. 128/260 |
| 4,092,983 | * | 6/1978 | Slivenko ........................... 128/214 R |
| 4,183,357 | * | 1/1980 | Bentley et al. ....................... 128/283 |
| 4,321,914 | * | 3/1982 | Begovac et al. ..................... 128/1 R |
| 4,578,063 | * | 3/1986 | Inman et al. ......................... 604/175 |
| 4,955,861 | | 9/1990 | Enegren et al. . |
| 5,098,397 | * | 3/1992 | Svensson et al. ................... 604/175 |
| 5,242,415 | * | 9/1993 | Kantrowitz et al. ................. 604/175 |
| 5,306,255 | | 4/1994 | Haindl ................................. 604/175 |
| 5,741,234 | * | 4/1998 | Aboul-Hosn .......................... 604/174 |

FOREIGN PATENT DOCUMENTS 3742263    12/1987    (DE) .
0302076    12/1992    (EP) .

* cited by examiner

Primary Examiner—Richard K. Seidel
Assistant Examiner—Michael Hayes
(74) Attorney, Agent, or Firm—Dorsey & Whitney LLP

(57) ABSTRACT

Implantable cylindrical device for connecting a hose arranged outside of the human or animal body to a hose arranged inside of the said body, wherein an anchoring plate falling away peripherally from the skin surface is arranged around the cylindrical device. This allows the skin to unroll over the anchoring plate subject to a tilting moment of the port body.

25 Claims, 1 Drawing Sheet

PORT BODY FOR THE ADMINISTRATION OF DRUGS

PRIORITY CLAIM

This application claims priority of Swiss patent application 1997 0729/97, filed Mar. 26, 1997, which is hereby fully incorporated herein by reference.

BACKGROUND OF THE INVENTION

1. Field of the Invention

The invention refers to an implantable cylindrical device for connecting a hose outside of the human or animal body to a hose arranged inside the said body, wherein an anchoring plate falling away peripherally from the skin surface is arranged around the cylindrical device.

2. Description of the Related Art

U.S. Pat. No. 5,306,255 describes a subcutaneous implantable port body. A subcutaneous port body is covered completely by skin and normally remains inside the human body for several months or even years. The port body contains the port chamber. The port chamber, fully located inside the human or animal body, is sealed by a puncturable plastic membrane on the skin side, while a catheter leading to the drug release site is fixed on the side facing the interior of the body. In order to administer the drugs, the skin and membrane are punctured with a needle of an infusion set. The creates a continuous drug channel from the infusion set to the release site.

European Patent EP-B-0 302 076 describes a cylindrical, percutaneous implantable port body. In contrast to the subcutaneous port body, the percutaneous port body is not fully implanted in the human body but is fixed in the tissue in such a way that at least a certain area of the port body is not covered by skin. The center of this area contains a first aperture. A second aperture of the port body is located opposite the first aperture in the section of the port body completely surrounded by tissue. A catheter whose end is located at the site inside the body to which the drug is to be transported is connected to this aperture. The port body consists of two metal parts which are screwed together. The inside of the port body, the port chamber, contains a puncturable membrane, separating the two apertures. The external casing of the port body contains several radial grooves for laterally anchoring the port in the subcutaneous skin tissue, with the outermost groove being located directly under the surface of the skin. The port chamber is also anchored with a base plate in the tissue.

The disadvantages of the subcutaneous port are that the catheter can neither be changed nor mechanically cleaned without explanting the port. A further disadvantage is that the skin is always punctured in the same place. In the short term this is painful and in the long term this causes a perforation of the skin and membrane.

The disadvantages of the described percutaneous port are that it is very heavy and has a large visible external surface. The metal port body is furthermore easily noticeable because of its color. Installed port bodies contain a gap between the base plate and the port body which is difficult to clean and sterilize. This represents an infection hazard. The radial grooves are arranged and dimensioned in such a way that sharp edges and corners are created. In these areas an effective growing-in of the tissue cells and adequate cleaning of the surface is not possible. Due to a lack of a geometrical separating line between the skin surface and the uppermost groove, external body perspiration or dirt may directly enter the grooves. In extreme cases this may cause an infection and require the port to be explanted. A further disadvantage is that the components of the described port must be machined from solid material. The manufacturing costs are consequently high with any weight reduction measures incurring additional costs. Prior art anchorings also present the hazard that parts of the anchoring may project from the skin due to the effect of a tilting moment.

SUMMARY OF THE INVENTION

The invention aims to remedy this situation. It is the aim of the invention to develop a low-cost port whose housing is adapted to the body-shape and contains an interconnected casing surface and continuous transitional areas. The port should preferably be produced by injection molding and be biocompatible. The skin should be able to grow tightly around the port wall. The growing-in depths of the skin should be as even as possible and should be controllable from the port. The shape of the anchoring must be designed in such a way that no edges or other parts of the anchoring protrude from the patient's body in case of a tilting moment.

The invention solves the set task by providing an implantable cylindrical device for connecting a hose outside of the human or animal body to a hose arranged inside the said body, wherein an anchoring plate falling away peripherally from the skin surface is arranged around the cylindrical device.

The invention offers the principle advantages of producing a cheaper port body which can be cleaned better when in use, is retained better by the body due to the design of its external surface and rolls the skin over the anchoring areas in case of a tilting moment. The selected material, shape and surface structure of the port body facilitate a longer implantation period.

BRIEF DESCRIPTION OF THE DRAWINGS

A preferred embodiment of the invention is shown in the figures, in which.

DESCRIPTION OF THE PREFERRED EMBODIMENTS

Hereinafter the term "inside" will mean "within the human or animal body" and "outside" will mean "outside of the human or animal body."

Figure 1:
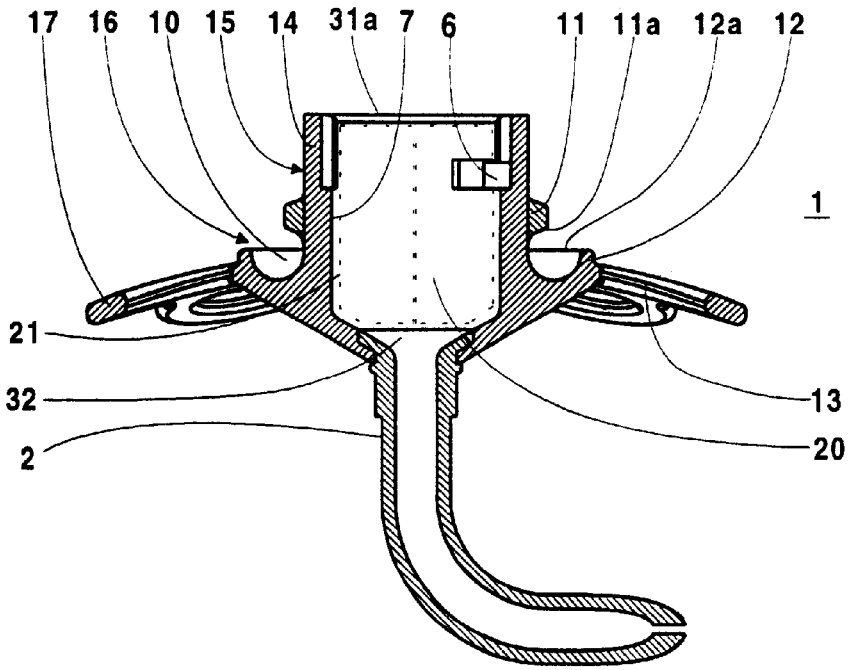
FIG. 1 represents a cross section of the port body according to the invention.
Figure 2:
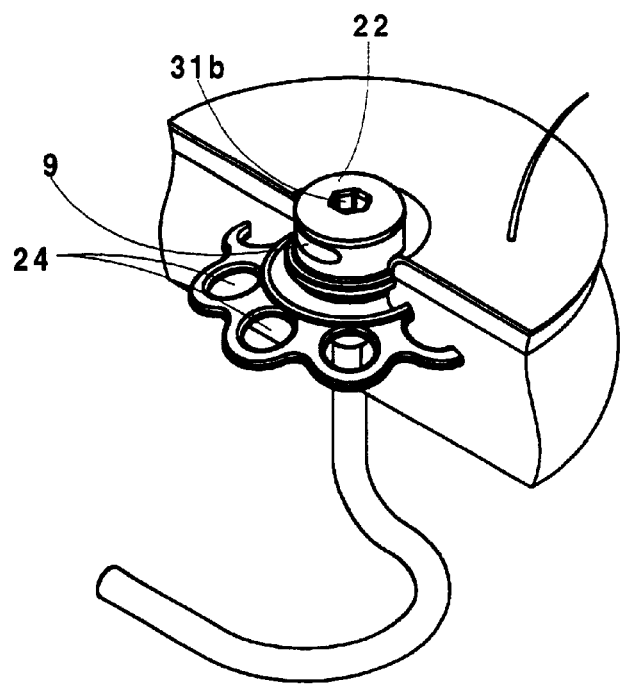
FIG. 2 represents a percutaneous port body according to the invention, located in a human or animal body.

As shown in FIGS. 1 and 2, the port body 1 can be divided into two main elements: a hollow cylindrical shaft 14 and a radial anchoring plate 13 arranged on the said shaft.

The port body 1 contains two opposing apertures 31a, 32. Aperture 31a, facing towards the outside and being an inlet aperture, corresponds to the internal diameter of the cylindrical port body 1. This opening 31a can be decreased in size by a lid 22 containing a smaller aperture 31b in its center. An infusion hose can be pushed through this small remaining aperture 31b into the inside of the port body. The second aperture 32, facing towards the inside and being an outlet aperture, serves to arrange a catheter 2 which moves the drug to be administered to the desired site inside the body.

In the area of the lid 22 the internal wall 7 of the cylindrical port body 1 contains bayonet cams 6 with an integrated locking groove, allowing the lid 22, containing corresponding counter-elements, to be secured to the port body.

The hollow cylindrical shaft 14 and the anchoring plate 13 are molded from a single biologically compatible plastic component. A flexible, self-closing, puncturable membrane 21 is arranged between the two apertures 31b and 32 filling and sealing the chamber 20 formed by the hollow cylindrical shaft 14.

The cylindrical port body 14 is divided into two areas, a shaft part 15, facing towards the outside, and an anchoring part 16, facing towards the inside. A protruding port fin 11 is radially arranged in between the two areas 15, 16.

The shaft part 15 is made of an inert material with a smooth surface structure. It ends in the outward facing aperture 31 on the side facing towards the outside and with the protruding port fin 11 on the side facing the anchoring part 16. In this area the skin cannot grow. When implanted, the shaft part 15 can be cleaned up to the port fin 11 from outside.

The anchoring part 16 consists of the port fin 11, an anchoring fin 12 protruding from the anchoring part 16 and the anchoring plate 13. Both the port fin 11 and the anchoring fin 12 contain a peripheral fin edge 11a, 12a. A channel-shaped, radial pocket 10 is formed between the port fin 11 and the anchoring fin 12 as the gap between the two peripheral fin edges 11a, 12a is considerably smaller than the cross-sectional diameter of the radial pocket 10 itself. Due to the gap formed between the two fin edges 11a, 12a, tissue cells can grow into the channel-shaped radial pocket 10. FIG. 2 illustrates growth of skin 50 in the radial pocket 10 and up to the protruding port fin 11 such that the device or a portion thereof is covered by or is underneath the skin 50.

The anchoring rib 12 may be part of the anchoring plate 13 or may be arranged separately from the said plate between the port fin 11 and the anchoring plate 13.

The anchoring part 16 is coated with a bio-active material and has a rough structure. This allows tissue to spread inside the pocket 10, and tissue cells can attached themselves to the rough 21 surface.

During the growth of the tissue into the radial pocket 10, the tissue wedges itself in the radial pocket 10 and ensures a flush connection between the tissue and the surface of the radial pocket 10.

The anchoring plate 13 is radially arranged around the anchoring part 16 of the hollow cylindrical shaft 14. The anchoring plate 13 has a plate-like shape falling away peripherally from the skin surface. As the anchoring plate 13 longitudinally extends from the cylindrical port body 1, it curves generally away from the skin 50 or toward aperture 32, as depicted in FIGS. 1 and 2. Peripheral edge 17 of the anchoring plate 13, therefore, is nearer aperture 32 than aperture 31a. In other words, a plane adjacent peripheral edge 17 is nearer a plane adjacent aperture 32 than a plane adjacent aperture 31a. During the effect of a tilting moment on the port body 1, the falling-away shape causes the skin to roll over the anchoring plate 13 instead of being pierced by its edge 17.

The anchoring plate 13 contains holes 24 through which the surround tissue grows to offer maximum retention.

In order to be able to open the port lid 22 once implanted, an installation aid recess 9 is arranged at the top end of the outer surface of the port shaft 15. A special tool grips into three such recesses 9 arranged at the same level, and the lid 22, whose aperture 31b is of a hexagonal shape, is released from its connection with the port body 14 by turning.

In a percutaneous port body 1 the lid 22 is preferably produced in a skin-like color as this area is visible from the outside. Naturally the entire port body may be produced in a skin-like color.

We claim:

1. An implantable device for implantation generally adjacent to a skin surface of a human or animal body for connecting a hose outside the human or animal body to a hose arranged inside the body, said device comprising a generally cylindrical port body and an anchoring plate arranged around the generally cylindrical port body, and extending generally radially therefrom, wherein, when the device is implanted, the anchoring plate is adapted to extend generally away from the skin surface,
   a radial port fin and an anchoring fin protruding from the anchoring plate, each fin having a peripheral fin edge, characterized in that a distance between the peripheral fin edge of the radial port fin and the peripheral fin edge of the anchoring fin is smaller than a cross-sectional diameter of a channel-shaped radial pocket formed by the fins.

2. The device according to claim 1, characterized in that the device is a molded plastic component.

3. The device according to claim 2, characterized in that a portion of the device has a color similar to that of the skin surface.

4. The device according to claim 3, characterized in that the device is adapted to be substantially covered completely by the skin surface.

5. The device according to claim 3, characterized in that an inlet aperture is adapted to be outside the skin surface.

6. The device according to claim 5, characterized in that when the hose is arranged inside the body it is adapted to seal an outlet aperture of the device and a lid containing a small aperture in its center, reduces in size the inlet aperture of the device.

7. The device according to claim 6, characterized in that a puncturable, flexible membrane sealing the inlet aperture is arranged inside the device.

8. An implantable device for implantation generally adjacent to a skin surface of a human or animal body for connecting a hose outside the human or animal body to a hose arranged inside the body, said device comprising a generally cylindrical port body and an anchoring plate arranged around the generally cylindrical port body, and extending generally radially therefrom, wherein, when the device is implanted, the anchoring plate extends generally away from the skin surface, further comprising two fins, each fin having a peripheral fin edge, said edges spaced from each other, characterized in that the distance between the two peripheral fin edges is smaller than a cross-sectional diameter of a channel-shaped radial pocket formed by the two fins.

9. The device according to claim 8, characterized in that the device is a molded plastic component.

10. The device according to claim 9, characterized in that the device or parts thereof have a color similar to that of the skin.

11. The device according to claim 10, characterized in that the device is adapted to be substantially covered by the skin surface.

12. The device according to claim 11, further comprising an inlet aperture and an outlet aperture, and characterized in that when the hose is arranged inside the body it is adapted to seal the outlet aperture of the device and a lid containing a small aperture in its center, reduces in size the inlet aperture of the device.

13. The device according to claim 12, characterized in that a puncturable, flexible membrane sealing the inlet aperture is arranged inside the device.

14. The device according to claim 10, characterized in that an inlet aperture is adapted to be outside the skin surface.

15. The device according to claim 14, characterized in that when the hose is arranged inside the body it is adapted to seal an outlet aperture of the device and a lid containing a small aperture in its center, reduces in size the inlet aperture of the device.

16. The device according to claim 15, characterized in that a puncturable, flexible membrane sealing the inlet aperture is arranged inside the device.

17. An implantable device for implantation in a human or animal body for connecting an infusion hose generally outside the body to a catheter generally inside the body, the implantable device comprising:

(a) a generally cylindrical, hollow shaft having an outside aperture and an inside aperture; and (b) an anchoring plate generally around the shaft, said anchoring plate having a periphery, wherein, when the device is implanted, said anchoring plate is adapted to extend generally toward the interior of the body and said periphery is adapted to be farthest from the exterior of the body, wherein the shaft includes an anchoring part carrying a radially protruding port fin and an anchoring fin, each fin having a periphery fin edge, wherein a radial pocket is formed between the port fin and the anchoring fin, wherein a gap between the peripheral fin edge of the port fin and the peripheral fin edge of the anchoring fin is smaller than a diameter of the radial pocket.

18. The implantable device of claim 17 wherein the anchoring plate contains a plurality of holes.

19. The implantable device of claim 17 wherein the anchoring plate includes a curved portion, whereby, when the device is implanted, the periphery is adapted to be farthest from the exterior of the body.

20. The implantable device of claim 19, wherein the anchoring plate curves along its radial extent, whereby when the device is implanted, the periphery is adapted to be farthest from the exterior of the body.

21. The implantable device of claim 19, wherein the anchoring plate curves uniformly along its radial extent, whereby, when the device is implanted, the periphery is adapted to be farthest from the exterior of the body.

22. An implantable device for implantation in a human or animal body generally adjacent to the skin for connecting an infusion hose outside the body to a catheter inside the body, the implantable device comprising:

a port body having a shaft part, an anchoring part, an inlet aperture, and an outlet aperture, wherein the anchoring part comprises a generally radially protruding port fin and an anchoring fin, each fin having a respective peripheral fin edge, said respective peripheral fin edges spaced from each other, and a radial pocket generally between the port fin and anchoring fin, wherein the space between the peripheral fin edges is less than a diameter of the radial pocket.

23. The implantable device of claim 22 further comprising an anchoring plate generally radially arranged around the anchoring part, said plate including a periphery, whereby, when the device is implanted, the periphery is adapted to be farther from the skin than the rest of the anchoring plate.

24. An implantable device for implantation in a human or animal body generally adjacent to the skin for connecting an infusion hose generally outside the body to a catheter generally inside the body, the implantable device comprising:

a generally hollow shaft having an outside end and an inside end and an outside opening adjacent to the outside end and an inside opening adjacent to the inside end, said shaft having an anchoring portion including a radial fin and an anchoring fin, and a channel-like pocket between the radial and anchoring fins; and a generally disc-shaped anchoring plate carried around the shaft in the anchoring portion, said anchoring plate having an annular portion adjacent to the shaft and a peripheral portion, and being curved along its radial extent, whereby, when the device is implanted, the peripheral portion is adapted to be farthest from the skin, wherein the radial fin and anchoring fin each have a respective fin edge, said fin edges spaced from each other, and wherein the pocket has a diameter greater than the space between the fin edges.

25. The device according to claim 24, wherein the shaft includes an outside shaft portion including at least one recess, whereby the device is adapted to be held during use.

* * * * *